US009321932B2

(12) United States Patent
De Jong

(10) Patent No.: US 9,321,932 B2
(45) Date of Patent: Apr. 26, 2016

(54) LATEX COMPRISING WATER AND A STYRENIC BLOCK COPOLYMER AND A PROCESS FOR PREPARING ARTICLES THEREFROM

(75) Inventor: Wouter De Jong, Almere (NL)

(73) Assignee: Kraton Polymers U.S. LLC, Houston, TX (US)

( * ) Notice: Subject to any disclaimer, the term of this patent is extended or adjusted under 35 U.S.C. 154(b) by 0 days.

(21) Appl. No.: 14/238,242

(22) PCT Filed: Aug. 9, 2012

(86) PCT No.: PCT/US2012/050142
§ 371 (c)(1),
(2), (4) Date: Feb. 11, 2014

(87) PCT Pub. No.: WO2013/025440
PCT Pub. Date: Feb. 21, 2013

(65) Prior Publication Data
US 2014/0171540 A1    Jun. 19, 2014

(30) Foreign Application Priority Data
Aug. 12, 2011   (NL) ..................................... 2007262

(51) Int. Cl.
| | |
|---|---|
| *C09D 109/08* | (2006.01) |
| *A61K 9/107* | (2006.01) |
| *A61D 19/00* | (2006.01) |
| *C09D 109/10* | (2006.01) |
| *C08K 5/00* | (2006.01) |
| *C09D 153/02* | (2006.01) |
| *A61B 19/04* | (2006.01) |
| *C08F 297/04* | (2006.01) |
| *C08J 5/02* | (2006.01) |
| *A61L 29/04* | (2006.01) |
| *A61L 29/08* | (2006.01) |
| *A61L 31/04* | (2006.01) |
| *A61L 31/10* | (2006.01) |
| *A61F 6/04* | (2006.01) |

(52) U.S. Cl.
CPC .............. *C09D 109/10* (2013.01); *A61B 19/04* (2013.01); *A61L 29/041* (2013.01); *A61L 29/085* (2013.01); *A61L 31/048* (2013.01); *A61L 31/10* (2013.01); *C08F 297/046* (2013.01); *C08J 5/02* (2013.01); *C08K 5/0025* (2013.01); *C09D 153/02* (2013.01); *C09D 153/025* (2013.01); *A61F 6/04* (2013.01); *C08J 2353/02* (2013.01)

(58) Field of Classification Search
CPC .... C08L 53/02; C09D 109/08; C09D 153/02; C08K 5/0025; C08K 3/06; C08F 297/046; A61F 6/04; A61B 19/04; A61L 31/048

USPC ................. 523/105; 524/836; 525/314, 332.6
See application file for complete search history.

(56) References Cited

U.S. PATENT DOCUMENTS

| | | | |
|---|---|---|---|
| 3,238,173 A | 3/1966 | Bailey et al. | |
| 3,265,765 A | 8/1966 | Holden et al. | |
| 3,360,599 A | 12/1967 | Nyberg et al. | |
| 5,232,987 A | 8/1993 | Sakakibara et al. | |
| 5,286,783 A | 2/1994 | Hisaki et al. | |
| 5,563,204 A | 10/1996 | Speth et al. | |
| 5,932,649 A | 8/1999 | Hergenrother et al. | |
| 6,469,104 B1 | 10/2002 | Colvin et al. | |
| 8,207,386 B2 | 6/2012 | Inoue et al. | |
| 2009/0234064 A1 | 9/2009 | Wang et al. | |
| 2010/0204397 A1 | 8/2010 | Kobayashi et al. | |
| 2011/0178234 A1 | 7/2011 | Wang et al. | |
| 2012/0021155 A1* | 1/2012 | Chen et al. .................. | 428/36.8 |
| 2013/0172445 A1 | 7/2013 | Wang et al. | |

FOREIGN PATENT DOCUMENTS

| | | |
|---|---|---|
| EP | 1731562 A1 | 12/2006 |
| WO | 9415997 A1 | 7/1994 |
| WO | 2007017368 A1 | 2/2007 |

OTHER PUBLICATIONS

Legge, N.R.; Holden, G. and Schroeder, H.E., Chapter 3 Thermoplastic Elastomers, A Comprehensive Review (ISBN 3-446-14827-2 Carl Hanser, Verlag, Munich, Vienna, New York 1987).
International Search Report of PCT/US2012/050142 dated Oct. 12, 2012.
Supplementary European Search Report, dated Apr. 4, 2015.
Korea preliminary rejection dated Sep. 11, 2015.

* cited by examiner

*Primary Examiner* — Tae H Yoon
(74) *Attorney, Agent, or Firm* — Clements Bernard PLLC; Leslie Streeter

(57) ABSTRACT

Articles with enhanced tensile strength and comfort are prepared from a latex comprising water and a styrenic block copolymer, wherein the styrenic block copolymer has 2 or more poly(vinyl aromatic) blocks and at least one block of polymerized conjugated diene, wherein the styrenic block copolymer has a weight average molecular weight of 150,000 to 250,000, the poly(vinyl aromatic) blocks have a weight average molecular weight ranging from 9,000 to 15,000, and the content of poly(vinylaromatic) blocks in the styrenic block copolymer ranges from 8 to 15% wt, based on the total styrenic block copolymer, by a process which comprises coating a surface with the latex to obtain a film, wherein the latex comprises a vulcanizing agent. The invention also provides a latex comprising such a styrenic block copolymer and a vulcanizing agent, as well as a styrenic block copolymer that is particularly suitable for use in such a latex.

11 Claims, No Drawings

LATEX COMPRISING WATER AND A STYRENIC BLOCK COPOLYMER AND A PROCESS FOR PREPARING ARTICLES THEREFROM

BACKGROUND OF THE INVENTION

The present invention relates to a latex comprising water and a styrenic block copolymer and to a process for preparing articles therefrom. In particular, the present invention relates to a process for preparing articles from a latex that comprises a particular styrenic block copolymer and wherein a surface is coated with the latex to obtain a film from which a thin article with improved tensile strength in combination with enhanced comfort can be obtained.

Natural rubber latex concentrates have been used for the manufacturing of rubber-dipped articles, adhesives, rubber thread, foam rubber etc. Natural rubber latex is in particular used for the manufacture of dipped articles such as: household gloves, examination gloves, industrial gloves, surgical gloves, catheters, teats and soothers, breather bags, tubing, balloons and condoms. When these articles are made by dipping it means that a surface or mould is dipped into the latex, thereby obtaining a coating of the rubber on the surface or on the mould.

Synthetic latices based on isoprene rubber are a very convenient replacement for natural rubber, as they do not suffer from the various allergens found in natural rubber. On the other hand, the production of high quality isoprene rubber and latices thereof is not easy. It thus remains of interest to find a synthetic latex that is relatively easy to make, free of allergens, that may be used for the preparation of dipped articles, and gloves, catheters and condoms in particular, with an improved balance of properties.

For instance, from U.S. Pat. No. 3,360,599 the preparation of high tensile strength films is known, made by annealing latices of A-B-A type block copolymers. In these block copolymers A represents a non-elastomeric polymer block, e.g. from lower olefins or a mono-vinyl arene, and B is an elastomeric polymer block, e.g. from a conjugated diene. Block copolymers according to this reference exhibit what are referred to as "self-curing" properties. By this is meant that the block copolymer exhibits the properties normally met in an elastomer which has been cured with the usual vulcanizing agents such as sulfur-containing compounds. The absence of a vulcanizing agent in such polymers is of great utility for many purposes, such as in the formation of molded articles, films, coatings or impregnated articles or in the preparation of latices, paints or adhesives.

From the even earlier U.S. Pat. No. 3,238,173, it was known that synthetic rubbers of the type A-B-A are self-vulcanizing rubbers. Latices containing such rubbers were found useful, e.g. in the preparation of dipped goods.

The above two references clearly show that in the preparation of dipped articles A-B-A type block copolymers are typically used without vulcanization packages.

Moreover, it is important that the articles made of synthetic rubber have a sufficiently high strength. For instance, in WO 2007/017368 it is described that one difficulty in the field of gloves for example, is the production of thin elastomeric articles having a high tensile strength. The solution that was found in WO 2007/017368 was the use of a specific vulcanization package that ensured that dipped articles from isoprene rubbers could be obtained with satisfactory tensile strength. The synthetic rubber used in this reference is not a self-curing type polymer of the type A-B-A.

This was a major improvement since the requirements for unaged surgical gloves dipped from natural rubber and synthetic rubber latices are specified in ASTM D3577. The mechanical requirements are tensile strength, ultimate elongation and stress at 500% elongation (also referred to as 500% modulus) measured according to ASTM D412. These requirements are listed in the table 1 below.

TABLE 1 requirements for surgical gloves

| Type | Tensile strength minimum value | Ultimate elongation minimum value | Stress at 500% elongation maximum value |
|---|---|---|---|
| I (natural rubber) | 24 MPa | 750% | 5.5 MPa |
| II (synthetic rubber) | 17 MPa | 650% | 7.0 MPa |

High-strength films prepared from aqueous dispersions of block copolymers of vinyl aromatic monomers and conjugated dienes are known from U.S. Pat. No. 5,563,204. It describes an aqueous dispersion comprising one or more block copolymers of the formula A-B-Xm-(B-A)n wherein each A polymer block consists essentially of a monovinylidene aromatic monomer, such as styrene, and each B block consists of a conjugated diene, such as isoprene. The blocks A have a weight average molecular weight from 8,000 to 15,000, each block B has a weight average molecular weight of 30,000 to 200,000, and the average A block content in the block copolymer may be 5 to 25% wt. These dispersions are capable of forming a free-standing, coherent, elastomeric, solid film which, after drying and annealing at 80° C. for 30 minutes, demonstrates a tensile strength of about 11.0 MPa or greater. These dispersions are stated to be suitable for use in the manufacture of surgical gloves, condoms, catheters, balloons and other thin elastomeric articles.

High strength, however, is not the only issue. Another factor that is as important in the manufacture of gloves, condoms and catheters, is comfort. Merely increasing the tensile strength is not sufficient if this causes discomfort to the users. The problem underlying the current invention is to increase strength whilst at least maintaining comfort.

In the requirements for surgical gloves according to ASTM D3577 the stress at 500% elongation is used to indicate stiffness and flexibility. However, it can hardly predict these comfort-related properties at low percentages of elongation during the actual use of the gloves. A much better parameter to indicate flexibility and softness is measurement of stress at very low values of elongation, such as the Young's modulus, being the modulus at zero percent elongation. Another factor is the thickness of the film which also affects the feeling of comfort during use. Evidently, the film thickness may be influenced by concentration of the rubber in the latex or the application methods, including number of times that the article is dipped and/or the duration of each dipping. Evidently, when an industrial process is being applied, it would be advantageous if thinner films could be prepared without unnecessary amendments to the process. It has now been found that if one goes against 50 years of practice in the preparation of dipped goods from a latex of block copolymers and one subjects a latex of specific block copolymers of vinyl aromatic monomers and conjugated dienes to vulcanisation, an article is obtained with improved tensile strength, which moreover has good or even enhanced comfort-related properties. It appears that thinner films may be obtained from such a latex.

SUMMARY OF THE INVENTION

Accordingly, the present invention provides a latex comprising water, a styrenic block copolymer, wherein the styrenic block copolymer has 2 or more poly(vinyl aromatic) blocks and at least one block of polymerized conjugated diene, wherein the styrenic block copolymer has a weight average molecular weight of 150,000 to 250,000, the poly (vinyl aromatic) blocks have a weight average molecular weight ranging from 9,000 to 15,000, and the content of poly(vinylaromatic) blocks in the styrenic block copolymer ranges from 8 to 15% wt, based on the total styrenic block copolymer, and a vulcanising agent.

The invention further provides a process for preparing articles from such a latex, which comprises coating a surface with the latex to obtain a film. Suitably the film thus obtained is vulcanised.

DETAILED DESCRIPTION OF THE INVENTION

Vulcanization of natural rubber and polyisoprene, which both require curing, is well known in the art. The vulcanization according to the present invention may be carried out using ingredients and conditions common in the vulcanization of natural and synthetic polydiene rubbers. Thus, sulphur compounds may be used to create cross-linking between the unsaturated bonds in the rubber chains of the B blocks. As is known from, e.g., WO 2007/017368 it is also possible to use one or more other additives, generally known as accelerators. Therefore, it is preferred to use in the present process a sulphur compound and optionally one or more accelerators. The sulphur compound may be any suitable sulphur-donating compound and is suitably selected from the group consisting of sulphur, thiuram sulphides, such as tetramethylthiuram disulfide, tetraethylthiuram disulfide, tetrabutylthiuram disulfide, tetrabenzylthiuram disulfide, dipentamethylene thiuram hexasulfide, dipentamethylene thiuram tetrasulfide, dithiodimorpholine, caprolactam disulfide, dialkylthiophosphoryl disulfide and mixtures thereof. For convenience's reasons sulfur is advantageously used. Suitable vulcanization conditions include exposure to a temperature from about 40 to about 200° C. for a period ranging from 1 to 60 minutes.

It is very suitable to include accelerators in the vulcanisation process for the purpose of reducing the vulcanizing time or increasing the vulcanization rate. The accelerators used in the vulcanization step are conventional accelerators that are typically used for the preparation of gloves and condoms and the like from isoprene rubber latex. These curing agents already meet the stringent requirements for use in surgical gloves, food contact and use in condoms and the like. These accelerators are suitably selected from the group consisting of a sulphenamide compounds, thiazole compounds, thiuram compounds, dithiocarbamates, xanthates and guanidines. Examples of these compounds include N-cyclohexyl-2-benzothiazyl sulfenamide, condensation product of n-butylaldehyde and aniline, zinc-2-mercaptobenzothiazole, diisopropylxanthogen polysulphide, zinc diethyldithiocarbamate and zinc di-isononyldithiocarbamate. A further suitable accelerator is diphenylguanidine, as disclosed in WO 2007/017368.

Other additives may also be added to the reaction mixture. Such additives include antioxidants, such as hindered phenolic compounds. e.g., the butylated reaction product of p-cresol and dicyclopentadiene (available as Wingstay L), butylated phenol and octylated phenol, fillers, activators, such as alkaline earth metal oxides or zinc oxide, dispersion stabilisers, such as alkali metal or alkaline earth metal caseinate, sodium lauryl sulphate and sorbitan fatty acid esters and a surfactant or combination of surfactants.

The amount of the sulphur compound may vary. Typically the amount by weight of sulphur compound will be from 0.2 to 4 parts by weight per hundred parts by weight of the combination of water and styrenic block copolymer ("phr"). The amounts by weight of the accelerator may suitably vary from 0.1 to 1.0 part per hundred parts of the water and styrenic block copolymer combination. Surprisingly, the process of the present invention can efficiently be carried out with a relatively low amount of sulphur compound. Therefore, the amount of sulphur in the vulcanization ranges advantageously from 0.2 to 1 phr. It will be evident that low amounts of sulphur and accelerators are advantageous since the lower the amount is, the less likelihood for a significant allergic reaction is.

The vulcanization may generally be carried out by subjecting a latex that comprises the sulphur compound, to heating. This will make the sulphur react with the unsaturation in the polymer chains of the styrenic block copolymer, thereby creating crosslinkings. It is also convenient to have the composition comprising the latex and the sulphur compound and optionally other additives on a heated surface to accomplish the vulcanising reaction.

Styrenic block copolymers are known and commercially available, for instance from Kraton Polymers LLC and other companies. In the current invention, a single styrenic block copolymer may be used, or a combination of styrenic block copolymers. In the process of the present invention, the styrenic block copolymer is preferably of the general formula A-B-A, wherein each block A independently is a poly(vinyl aromatic) block, and wherein block B is a block of polymerized conjugated diene, wherein each block independently may be a homopolymer block or a copolymer block, and wherein block B may be partly hydrogenated. Suitably, the block B is not hydrogenated; it suitably contains at least 90% of its original unsaturation.

Preferably each poly(vinyl aromatic) block independently is a block composed mainly of polymerized vinyl aromatic monomer. The poly(vinyl aromatic) block may contain a copolymerizable monomer, but preferably in an amount of less than 5% by weight based on the weight of the poly(vinyl aromatic) block. The poly(vinyl aromatic) block may for instance comprise less than 5 wt % of a conjugated diene such as butadiene or isoprene. The vinyl aromatic monomer is preferably styrene. Hence, each poly(vinyl aromatic) block independently is preferably a polystyrene block, containing less than 5 wt % of copolymerizable monomer, based on the weight of poly(vinyl aromatic) block.

Preferably each polydiene block B is a block composed mainly of polymerized conjugated diene. It may contain remnants of a coupling agent. The polydiene block may be partially hydrogenated, for instance up to 80% of the original unsaturation. The block may contain a mixture of conjugated dienes that are copolymerized. In addition, the block may contain a copolymerizable monomer other than a conjugated diene that is copolymerized, but preferably in an amount of less than 5% by weight based on the weight of the block. The polydiene block B may for instance comprise up to 5 wt % of a vinyl aromatic monomer such as styrene. Preferably, the conjugated diene used for the preparation of block conjugated diene is butadiene or isoprene or a mixture of butadiene and isoprene, more preferably isoprene. Hence, each block of polymerized conjugated diene is preferably a polyisoprene block, containing less than 5 wt % of copolymerizable monomer, based on the weight of block of polymerized conjugated diene.

The styrenic block copolymer may be prepared in any way known in the art. One possible method for the preparation includes the production of a poly(vinyl aromatic) block A and add thereto a block of polymerised conjugated diene B. The resulting diblock A-B may subsequently be coupled to a triblock by using a bifunctional coupling agent, or to a star-shaped block copolymer by using a multi-functional coupling agent such as a core of poly(divinylbenzene) or a silicon compound, such as $SiCl_4$. Another preparation method includes sequential polymerisation by polymerising a block A first, polymerising subsequently a block B to the block A obtained, then again a block A, and so forth.

DESCRIPTION OF THE INVENTION

In the process of the present invention, the preferred styrenic block copolymer has the general formula A-B-A wherein each A represents a polystyrene block and B represents an polyisoprene block. More preferably the styrenic block copolymer is a sequential SIS block copolymer, wherein S represents a polystyrene block and I a polyisoprene block. A sequential block copolymer is made by sequentially preparing a block copolymer comprising blocks A, B and then A, and therefore differs from a coupled block copolymer that is made by sequentially preparing a diblock copolymer comprising blocks A, ½ B and then coupling the diblock copolymer.

The styrenic block copolymer has a poly(vinyl aromatic) content of from 8 to 15 wt %, preferably 9 to 14 wt %, based on the weight of the styrenic clock copolymer. Moreover, the styrenic block copolymer has a weight average molecular weight (determined by GPC) of from 150,000 to 250,000, preferably from 170,000 to 220,000. Each poly(vinyl aromatic) block of the styrenic block copolymer has a weight average molecular weight of from 8.000 to 15,000, preferably from 9,000 to 14,000.

The styrenic block copolymer may be prepared by processes known in the art, using an organolithium compound as initiator with sequential polymerization of the monomers styrene, isoprene and styrene, respectively, in a solvent. A-B-A block copolymers are for instance described in U.S. Pat. No. 3,265,765. Sequential polymerization is for instance described in Chapter 3 of Thermoplastic Elastomers, A comprehensive review, edited by N. R. Legge. G. Holden and H. E. Schroeder (ISBN 3-446-14827-2 Carl Hanser Verlag, Munich, Vienna, N.Y. 1987).

Suitably, the styrenic block copolymer that is used in the process according to the present invention has been prepared by sequential polymerization of (i) a vinyl aromatic monomer or a mixture (a) composed for at least 95 wt % of a vinyl aromatic monomer and at most 5 wt % of a copolymerizable monomer, based on the weight of the mixture (a);

(ii) a conjugated diene or a mixture (b) composed for at least 95 wt % of a conjugated diene, and at most 5 wt % of a copolymerizable monomer based on the mixture (b), and (iii) a vinyl aromatic monomer or a mixture (c) composed for at least 95 wt % of a vinyl aromatic monomer and at most 5 wt % of a copolymerizable monomer based on the mixture (c).

For the preparation of the synthetic latex anionic, cationic or non-ionic surfactants or combinations thereof may be used. The surfactant is present in a sufficient amount to emulsify the styrenic block copolymer (or copolymers if a combination of block copolymers is used). To produce a synthetic latex, the styrenic block copolymer, usually in the form of a solution in an organic solvent (also referred to as a cement), is dispersed in water using a suitable surfactant or a combination of surfactants and the organic solvent is removed. A suitable procedure is disclosed in, e.g., U.S. Pat. No. 3,238,173.

For the preparation of thin walled rubber articles preferably a synthetic latex is used having a solids content of from 20 to 80%, more preferably of from 30 to 70% by weight. Most preferably the synthetic latex has a solids content of from 35 to 65% by weight.

To prepare a thin walled rubber article from the latex, such as a film, a suitable surface is coated with the latex and the water thereafter removed by evaporation. A second or further layer may be provided in the same manner to achieve thicker films. The film resulting from the foregoing procedure is dried and vulcanised, if desired, by any suitable technique. Heating is typically used, with preferred temperatures for drying and vulcanisation varying from 25 to 130° C.

To prepare a dipped article, a similar process is used, wherein a mould is dipped into the latex. In a preferred embodiment of the process for making a thin walled article, the mould is dipped into the latex. The dip-coated mould is then removed from the latex and dried. The mould may be dip coated more than once in the same latex. In an alternative process a mould is dip-coated in a first latex, followed by (air) drying and dip-coating in a second latex and so forth. In this way balloons, and condoms may be made. In a different embodiment, the mould may be dipped in a dispersion of a coagulant, the coagulant on the surface of the mould may be dried, and subsequently, the mould is dipped into the rubber latex. The latter manner is especially used for the manufacture of gloves.

In addition to the vulcanising agent and optional other additives that have been described above, the latex may comprise various other additives such as oils, co-solvents, waxes, colorants, tackifiers, fillers, release agents, anti-blocking agents and other conventional additives.

As indicated above, the present invention also provides a latex comprising water, a styrenic block copolymer, wherein the styrenic block copolymer has 2 or more poly(vinyl aromatic) blocks and at least one block of polymerized conjugated diene, wherein the styrenic block copolymer has a weight average molecular weight of 150,000 to 250,000, the poly(vinyl aromatic) blocks have a weight average molecular weight ranging from 9,000 to 15,000, and the content of poly(vinylaromatic) blocks in the styrenic block copolymer ranges from 8 to 15% wt, based on the total styrenic block copolymer, and a vulcanising agent.

As indicated above, the vulcanising agent preferably comprises a sulphur compound and optionally, accelerators. The sulphur compounds may suitably be selected from the compounds mentioned above. The same holds for the accelerators and the amount of the components in the latex.

A further aspect of the present invention is directed to a styrenic block copolymer comprising 2 or more poly(vinyl aromatic) blocks and at least one block of polymerized conjugated diene, wherein the styrenic block copolymer has a weight average molecular weight of 150,000 to 250,000, the poly(vinyl aromatic) blocks have a weight average molecular weight ranging from 9,000 to 15,000, and the content of poly(vinylaromatic) blocks in the styrenic block copolymer ranges from 8 to 15% wt, based on the total styrenic block copolymer.

The present invention also specifically provides the article that has been obtained by the process for preparing an article from the latex as described above. Such articles are suitably glove, catheter or condom. The invention therefore also provides the use of any such article as glove, catheter or condom.

EXAMPLES

Additional features and advantages of the present invention are described in the following examples.

Test Methods:

Molecular weights were determined by GPC (Gel Permeation Chromatography) using a calibration curve based on mono-dispersed polystyrene standards such as is done according to ASTM 3536. The molecular weight of polymers measured using GPC so calibrated are styrene equivalent molecular weights. The styrene equivalent molecular weight may be converted to true molecular weight when the styrene content of the polymer and the vinyl content of the diene segments are known. The detector used is preferably a combination ultraviolet and refractive index detector.

Tests for physical properties were performed using ASTM D412 (92), die C. All tests were performed on an Instron 4465 tensile machine. Since the Young's modulus (at 0% elongation) of the very soft and flexible materials that were obtained in the experiments appeared very difficult to measure, the modulus of the synthetic lattices at low elongation (between 5 and 15%) was measured and the result was called "10% Young's modulus". The values in Example 1 represent average values measured on films during 7 days.

Example 1

A series of lattices were formed from isoprene rubber, polystyrene-polyisoprene rubber and polystyrene-polyisoprene-polystyrene block copolymers. Test specimens were prepared by first dipping stainless steel plates in a coagulant solution and, after drying, in the polymer latex. The objective was to form a uniform layer of the latex as it precipitated onto the plates. The forms with the adhered latex were then air-dried at room temperature to evaporate the water from the thin elastomeric layer to yield a dry film. The films were then vulcanised in an oven at 110-130° C. for 15 minutes.

In the experiments two different vulcanisation packages were used, the compositions of which are described in the Table 2 below.

TABLE 2

Vulcanisation packages; amounts in part per 100 parts of water and rubber

| Compound | Package A | Package B |
|---|---|---|
| Sulphur | 0.63 | 1.25 |
| Sodium caseinate | 0.75 | 0.75 |
| Zinc diethyldithiocarbamate | 0.5 | 0.5 |
| Diphenyl guanidine | 0.5 | 1.0 |
| Wingstay L | 2.0 | 2.0 |

(a) A comparative test sample was prepared with Cariflex® IR 401 polyisoprene latex. This IR 401 is an isoprene rubber with a weight average molecular weight of 2,500,000 with a high cis content. This is the preferred polyisoprene rubber in WO 2007/07368. With this synthetic latex comprising vulcanisation package B, it was possible to achieve a tensile strength of 21.3 MPa, a tear strength of 35.4 N/mm and a "10% Young's modulus" of 0.18 MPa.

(b) The experiment of Example 1(a) was repeated with the sole difference that vulcanisation package A was included in the latex. A tensile strength of 17.6 MPa and a "10% Young's modulus" of 0.17 MPa were obtained.

(c) The experiment of Example 1(a) was repeated with the difference that a polyisoprene rubber with a weight average molecular weight of 500,000 was used, the tensile strength drastically reduced to 15.4 MPa, and a "10% Young's modulus" of 0.14 MPa was obtained.

(d) A minor improvement is seen when a block copolymer comprising a polyisoprene block and a single styrene block (polystyrene content of 2.5%) is used. When (c) was repeated with a high cis, two block rubber with a molecular weight of 470,000 of the polyisoprene block and a molecular weight of 12,000 of the polystyrene block, a tensile strength was found of 17.4 MPa, and a "10% Young's modulus" of 0.17 MPa.

(e) A comparative test sample was prepared with Kraton® D1160. D1160 is an SIS type block copolymer with a molecular weight of 117,000 and a molecular weight of each of the polystyrene blocks of 11.000. The polystyrene content is 19 wt %. Vulcanization package B was applied. With this synthetic latex it was possible to achieve a tensile strength of 22.6 MPa, but with a "10% Young's modulus" that is twice as high as that of IR 401, of 0.37 MPa. This adversely affects the comfort of dipped articles made from this latex (f) Experiment of Example 1(e) was repeated with the difference that vulcanisation package A was included in the latex. A tensile strength of 26.0 MPa and a "10% Young's modulus" of 0.38 MPa were obtained.

(g) The experiment of Example 1(e) was repeated but without the addition of a vulcanisation package. A tensile strength of 22.2 MPa and a "10% Young's modulus" of 0.33 MPa were obtained.

(h) The experiment of Example 1(e) was repeated, with an SIS type block copolymer with a weight average molecular weight of the styrenic block copolymer of 182,000 and a molecular weight of each of the polystyrene blocks of 12,000. The polystyrene content is 14 wt %. Vulcanization package A was used. With this synthetic latex it was possible to achieve a tensile strength of 27.2 MPa and a "10% Young's modulus" of only 0.25 MPa.

(i) The experiment of Example 1(h) was repeated, but without the addition of a vulcanisation package. A tensile strength of 22.3 MPa and a "10% Young's modulus" of 0.24 MPa were obtained.

(j) The experiment of Example 1(h) was repeated, with an SIS type block copolymer with a weight average molecular weight of the styrenic block copolymer of 193,000 and a molecular weight of each of the polystyrene blocks of 11,000. The polystyrene content is 12 wt %. Vulcanization package A was used. With this synthetic latex it was possible to achieve a tensile strength of 33.9 MPa and a "10% Young's modulus" of only 0.25 MPa.

(k) The experiment of Example 1(j) was repeated, but without the addition of a vulcanisation package. A tensile strength of 21.0 MPa and a "10% Young's modulus" of 0.25 MPa were obtained.

(l) The experiment of Example 1(h) was repeated, with an SIS type block copolymer with a weight average molecular weight of the styrenic block copolymer of 206,000 and a molecular weight of each of the polystyrene blocks of 11,000. The polystyrene content is 11 wt %. Vulcanization package A was used. With this synthetic latex it was possible to achieve a tensile strength of 29.4 MPa and a "10% Young's modulus" of only 0.22 MPa.

(m) The experiment of Example 1(l) was repeated, but without the addition of a vulcanisation package. A tensile strength of 22.0 MPa and a "10% Young's modulus" of 0.21 MPa were obtained.

(n) The experiment of Example 1(h) was repeated, with an SIS type block copolymer with a weight average molecular weight of the styrenic block copolymer of 210,000 and a molecular weight of each of the polystyrene blocks of 10,000. The polystyrene content is 10 wt %. Vulcanization package A was used. With this synthetic latex it was possible to achieve a tensile strength of 23.9 MPa and a "10% Young's modulus" of only 0.24 MPa.

(o) The experiment of Example 1(l) was repeated, but without the addition of a vulcanisation package. A tensile strength of 21.0 MPa and a "10% Young's modulus" of 0.22 MPa were obtained.

The results are summarised in the following Table 3.

TABLE 3

Results of the experiments (I = polyisoprene; S = polystyrene; Mw S = mol weight of styrene blocks, PSC = polystyrene content; T.S. = tensile strength, 10% Ym = "10% Young's modulus")

| Exp. | Polymer | Mw | Mw S | PSC, % wt | Vulcanisation package | T.S., MPa | 10% Ym, MPa |
|---|---|---|---|---|---|---|---|
| (a) | I | 2,500,000 | — | — | B | 21.3 | 0.18 |
| (b) | I | 2,500,000 | — | — | A | 17.6 | 0.17 |
| (c) | I | 500,000 | — | — | B | 15.4 | 0.14 |
| (d) | SI | 482,000 | 12,000 | 2.5 | B | 17.4 | 0.17 |
| (e) | SIS | 117,000 | 11,000 | 19 | A | 22.6 | 0.37 |
| (f) | SIS | 117,000 | 11,000 | 19 | B | 26.0 | 0.38 |
| (g) | SIS | 117,000 | 11,000 | 19 | — | 22.2 | 0.33 |
| (h) | SIS | 182,000 | 12,000 | 14 | A | 27.2 | 0.25 |
| (i) | SIS | 182,000 | 12,000 | 14 | — | 22.3 | 0.24 |
| (j) | SIS | 193,000 | 11,000 | 12 | B | 33.9 | 0.25 |
| (k) | SIS | 193,000 | 11,000 | 12 | — | 21.0 | 0.25 |
| (l) | SIS | 206,000 | 11,000 | 11 | A | 29.4 | 0.22 |
| (m) | SIS | 206,000 | 11,000 | 11 | — | 22.0 | 0.21 |
| (n) | SIS | 210,000 | 10,000 | 10 | A | 23.9 | 0.24 |
| (o) | SIS | 210,000 | 10,000 | 10 | — | 21.0 | 0.22 |

Experiments (h), (j), (l) and (n) are experiments according to the invention. The results clearly show that when a styrenic block copolymer is used and the molecular weight, the styrene content and the styrene molecular weight are within the ranges of the present invention and when a vulcanising agent is added to the latex, articles with a high tensile strength are obtained whilst their stress at small elongation is low and not affected by the vulcanisation. Moreover, the tensile strength is significantly higher compared to articles prepared without vulcanisation. These lattices therefore provide a surprisingly improved tensile strength with enhanced comfort properties.

Experiments (e), (f) and (g) show that when the polystyrene content is outside the claimed range, the improvement in strength is moderate whereas the increase in 10% Young's modulus is significant and considerably more than in the experiments according to the present invention.

Example 2

To show the effect of vulcanization on the film thickness the lattices of experiments 1(h) and 1(i), and 1(n) and 1(o) were tested using identical dipping conditions. The latex into which the stainless steel plates were dipped, contained 40% wt of styrenic block copolymer. The plates were dipped once during 30 seconds. Vulcanisation was conducted as in Example 1. The film thickness was measured immediately after vulcanisation. When the latex did not contain a vulcanising agent the film thickness was measured after annealing.

The results are shown in the following Table 4.

TABLE 4

Film thickness

| Latex of experiment | Film thickness, mm |
|---|---|
| 1(h) | 0.183 |
| 1(i) | 0.248 |
| 1(n) | 0.196 |
| 1(o) | 0.261 |

These results clearly show that vulcanisation also results in thinner films at comparable conditions.

Example 3

To show the effect of the higher strength after vulcanization of the lattices according to this invention, thin films were dipped from lattices of example (a) and (l). To obtain thin films, glass formers were used. The glass formers were not coated with a coagulant but dipped directly into the lattices for 2 or 3 times. Each layer was cured in an oven for 5 minutes at 120° C. and after the last layer was applied the film was cured for 10 minutes at 120° C. Film thickness and tensile strength were measured.

The results are shown in the following Table 5.

TABLE 5

Film thickness and tensile strength

| Latex of experiment | Number of dips | Film thickness (mm) | Tensile strength (MPa) |
|---|---|---|---|
| 1(a) | 2 | 0.053 | 18.5 |
|  | 3 | 0.087 | 20.0 |
| 1(l) | 2 | 0.031 | 21.0 |
|  | 3 | 0.046 | 26.7 |

These results clearly show that films dipped from the lattices according to the present invention are thinner and have higher strength compared to films dipped from synthetic polyisoprene latex.

The invention claimed is:

1. A latex comprising water and a styrenic block copolymer, wherein the styrenic block copolymer has 2 or more poly(vinyl aromatic) blocks, said poly(vinyl aromatic) blocks are a polystyrene block, containing less than 5 wt % of copolymerizable monomer, based on the weight of poly(vinyl aromatic) block and at least one block of polymerized conjugated diene, said conjugated diene is a polyisoprene block, containing less than 5 wt % of copolymerizable monomer, based on the weight of block polymerized conjugated diene, wherein the styrenic block copolymer has a weight average molecular weight of 170,000 to 220,000, the poly(vinyl aromatic) blocks have a weight average molecular weight ranging from 9,000 to 14,000, and the content of poly(vinylaromatic) blocks in the styrenic block copolymer ranges from 9 to 14% wt, based on the total styrenic block copolymer, and a vulcanising agent.

2. A latex according to claim 1, wherein the vulcanising agent comprises a sulphur compound and, optionally, one or more accelerators.

3. A latex according to claim 2, wherein one or more accelerators are used and are selected from the group consisting of sulphenamide compounds, thiazole compounds, thiuram compounds, dithiocarbamates, xanthates and guanidines.

4. A latex according to claim 2, wherein the sulphur compound has been selected from the group consisting of sulphur, thiuram sulphides, dithiodimorpholine, caprolactam disulphide, dialkylthiophosphoryl disulphide, diisopropylxanthogen polysulphide, and mixtures thereof.

5. A latex according claim 2, wherein the amount of the sulphur compound ranges from 0.2 to 4 parts by weight per hundred parts by weight of the combination of water and styrenic block copolymer.

6. A latex according to claim 1, wherein the styrenic block copolymer is of the general formula A-B-A, wherein each block A independently is a poly(vinyl aromatic) block, and wherein block B is a block of polymerized conjugated diene, wherein each block independently is a homopolymer block or a copolymer block, and optionally a block B is partly hydrogenated.

7. A latex according to claim 1, wherein the styrenic block copolymer has been prepared by sequential polymerization of
(i) a vinyl aromatic monomer or a mixture (a) composed for at least 95 wt % of a vinyl aromatic monomer and at most 5 wt % of a copolymerizable monomer, based on the weight of the mixture (a),
(ii) a conjugated diene or a mixture (b) composed for at least 95 wt % of a conjugated diene, and at most 5 wt % of a copolymerizable monomer based on the weight of the mixture (b), and
(iii) a vinyl aromatic monomer or a mixture (c) composed for at least 95 wt % of a vinyl aromatic monomer and at most 5 wt % of a copolymerizable monomer based on the weight of the mixture (c).

8. The latex according to claim 1, wherein the latex comprises from 20 to 80% by weight of styrenic block copolymer, based on the weight of the combination of water and styrenic block copolymer.

9. A process for preparing articles from a latex according to claim 1, which process comprises coating a surface with the latex to obtain a film.

10. An article prepared from the latex of claim 1, in the form of a glove, catheter or condom.

11. Cured, vulcanized latex comprising a styrenic block copolymer comprising 2 or more poly(vinyl aromatic) blocks and at least one block of polymerized conjugated diene, wherein the styrenic block copolymer has a weight average molecular weight of 170,000 to 220,000, the poly(vinyl aromatic) blocks have a weight average molecular weight ranging from 9,000 to 14,000, and the content of poly(vinylaromatic) blocks in the styrenic block copolymer ranges from 9 to 14% wt, based on the total styrenic block copolymer, said cured, vulcanized latex has a tensile strength $\geq 23.9$ but $\leq 33.9$ MPa, and said latex has a 10% Young's Modulus $\geq 0.22$ but $\leq 0.25$ MPa, according to ASTM D412 and ASTM D3577.

* * * * *